(12) United States Patent
Bottaro et al.

(10) Patent No.: US 8,569,360 B2
(45) Date of Patent: Oct. 29, 2013

(54) COMPOSITIONS AND METHODS FOR INHIBITION OF HEPATOCYTE GROWTH FACTOR RECEPTOR C-MET SIGNALING

(76) Inventors: Donald P. Bottaro, Kensington, MD (US); Megan Peach, Ashburn, VA (US); Marc Nicklaus, Catonsville, MD (US); Nelly Tan, El Monte, CA (US)

(*) Notice: Subject to any disclaimer, the term of this patent is extended or adjusted under 35 U.S.C. 154(b) by 0 days.

(21) Appl. No.: 12/935,646

(22) PCT Filed: Mar. 31, 2009

(86) PCT No.: PCT/US2009/038915
§ 371 (c)(1),
(2), (4) Date: Jan. 28, 2011

(87) PCT Pub. No.: WO2009/124024
PCT Pub. Date: Oct. 8, 2009

(65) Prior Publication Data
US 2011/0281907 A1    Nov. 17, 2011

Related U.S. Application Data

(60) Provisional application No. 61/041,523, filed on Apr. 1, 2008.

(51) Int. Cl.
*A61K 31/352* (2006.01)
*C07D 311/82* (2006.01)

(52) U.S. Cl.
USPC .......................................... 514/454; 549/391

(58) Field of Classification Search
USPC .................... 514/297, 454; 549/391; 546/102
See application file for complete search history.

(56) References Cited

U.S. PATENT DOCUMENTS 6,162,610 A * 12/2000 Bronstein et al. ............ 435/7.92

FOREIGN PATENT DOCUMENTS

WO    WO 2004/020410    3/2004
WO    WO 2004/044219    5/2004

OTHER PUBLICATIONS

Wang et al., Spectrophotometric Study on the Quaternary Complex of Titanium (IV) with Secondary Ligands, 2,6,7-Trihydroxylphenyl-fluorone Derivatives and Cetyltrimethylammonium Bromide, 1992, Mikrochim. Acta, 108, 79-91.*
Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

Bellon et al., c-Met inhibitors with novel binding mode show activity against several hereditary papillary renal cell carcinoma-related mutationsJ. Biol. Chem. 283: 2675-2683, Feb. 2008.
Belmont P et al: "Acridine/acridone: A simple scaffold with a wide range of application in oncology" Expert Opinion on Therapeutic Patents 200811 GB, vol. 18, No. 11, Nov. 2008, pp. 1211-1224, XP002534465.
Cai Sui X: "Small molecule vascular disrupting agents: potential new drugs for cancer treatment." Recent Patents on Anti-Cancer Drug Discovery Jan. 2007, vol. 2, No. 1, Jan. 2007, pp. 79-101, XP002534464.
CAplus Registry Number: RN 871911-77-2, Accessed in STN Apr. 9, 2012.
Christensen et al., A selective small molecule inhibitor of c-Met kinase inhibits c-Met-dependent phenotypes in vitro and exhibits cytoreductive antitumor activity in vivo Cancer Research 63: 7345-7355, Nov. 2003.
Cui, J J., "Inhibitors targeting hepatocyte growth factor receptor and their potential therapeutic applications," Expert Opinion on Therapeutic Patents, vol. 17, No. 9, 2007, pp. 1035-1045, XP002530501.
Database Beilstein [Online] Elsevier Information Systems GMBH; Jan. 2009, XP002530507, Database Accession No. 11147104 (BRN) abstract & Yavari et al., Synthetic Communications, vol. 37, 2007, pp. 2593-2599.
Database Beilstein Elsevier Information Systems; Beilstein Registry No. 1264282 XPP002534467 abstract, 2009.
Database Medline [Online] US National Library of Medicine (NLM), Bethesda, MD, US; 1990, Database accession No. NLM2265456 Abstract & Sweatman T W et al: "Metabolism and elimination of rhodamine 123 in the rat." Cancer Chemotherapy and Pharmacology 1990, vol. 27, No. 3, 1990, pp. 205-210; XP-002534517.

(Continued)

*Primary Examiner* — Kristin Vajda
(74) *Attorney, Agent, or Firm* — Woodcock Washburn LLP

(57) ABSTRACT

Derivatives and analogs of inhibitors of receptor tyrosine kinase c-Met obtained by virtual screening, pharmaceutical compositions containing derivatives and analogs of c-Met inhibitors are provided. Methods of making derivatives and analogs of c-Met inhibitors and methods of use thereof are provided. Formula (I)

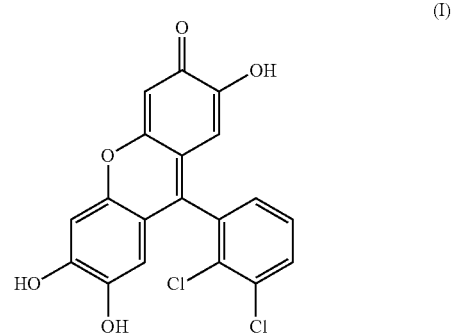

(I)

13 Claims, 11 Drawing Sheets

(56) References Cited

OTHER PUBLICATIONS

Database Registry [Online] Chemical Abstracts Service, Columbus, Ohio, US, Feb. 15, 2002, XP002530503, Database Accession No. RN: 392733-40-3, Abstract.
Database Registry [Online] Chemical Abstracts Service, Columbus, Ohio, US, Jan. 13, 2006, XP002530504, Database Accession No. RN: 871911-77-2, Abstract.
Database Registry [Online] Chemical Abstracts Service, Columbus, Ohio, US, Apr. 28, 2006, XP002530505, Database Accession No. RN: 882114-94-5, Abstract.
Database Registry [Online] Chemical Abstracts Service, Columbus, Ohio, US, Nov. 1, 2008, XP002530506, Database Accession No. 2063408403, Order Number: AKI-VT-00207511 & "AKOS Out of Stock Compounds" Nov. 1, 2008, AKOS-Consulting and Solutions GMBH RN: 882114-94-5.
Database Registry Chemical Abstracts Service, Columbus, Ohio, US; RN:690969-01-8 Jun. 9, 2004, XP002534466 abstract.
Fingl et al., 1975, In: The Pharmacological Basis of Therapeutics, Ch.1, p. 1.
Gao CF, Vande Woude GF, "HGF/SF-Met signaling in tumor progression." Cell Res. 15: 49-51, Jan. 2005.
Garcia-Echeverria et al., "ATP site-directed competitive and irreversible inhibitors of protein kinases" Medicinal Research Reviews 20: 28-57, Jan. 2000.
Gasteiger et al., "Automatic generation of 3D-atomic coordinates for organic moleculesTetrahedron" Computer Methodology 3: 537-547, 1990.
Gould et al., "Designing specific protein kinase inhibitors: insights from computer simulations and comparative sequence/structure analysis" Pharmacology & Therapeutics 93: 169-178, Feb.-Mar. 2002.
Ihlenfeldt et al., "Computation and management of chemical properties in CACTVS: An extensible networked approach toward modularity and compatibility," Journal of Chemical Information and Computer Sciences 34: 109-116, 1994.
International Search Report issued in PCT/US2009/038896, Jul. 8, 2009.
International Search Report issued in PCT/US2009/038915, Jul. 13, 2009.
Jones et al., "Development and validation of a genetic algorithm for flexible docking," Journal of Molecular Biology 267: 727-748, Apr. 1997.
Kim et al., "Design and synthesis of c-met kinase inhibitors based on an in silico screen-derived lead" Abstract MEDI-361 at 234th National American Chemical Society Meeting, Boston, MA, Aug. 19-23, 2007.
Lieberman, Lindenbaum: "ueber die Condensation des Oxyhydrochinoins mit Aldehyden" Chemische Berichte, 1904, pp. 2728-2737, XP002534462.
Lipinski et al., "Preparation of peptide and protein powders for inhalation," Advanced Drug Delivery Reviews 23: 3-25, Jun. 1997.
Ma et al., "c-Met: structure, functions and potential for therapeutic inhibition", Cancer and Metastasis Reviews 22: 309-325, Dec. 2003.
Milne GW, et al., "Molecular modeling in the discovery of drug leads", J Chem Inf Comput Sci. 36: 726-30, Jul.-Aug. 1996.
Mohamadi et al., "Macromodel—an integrated software system for modeling organic and bioorganic molecules using molecular mechanics," Journal of Computational Chemistry 11: 440-467, 1990.
Moriotti et al., "K252a inhibits the oncogenic properties of Met, the HGF receptor", Oncogene 21: 4885-4893, Jul. 2002.
Noble et al., "Protein kinase inhibitors: insights into drug design from structure" Science 303: 1800-1805, Mar. 2004.
Novac Olivia et al: Inhibitors of protein synthesis identified by a high throughput multiplexed translation screen. Nucleic Acids Research 2004, vol. 32, No. 3, 2004, pp. 902-915, XP002534463.
Peach, Megan L. et al., "Directed Discovery of Agents Targeting the Met Tyrosine Kinase Domain by Virtual Screening," Journal of Medicinal Chemistry, vol. 53, No. 4, Feb. 2009, pp. 943-951, XP002530502.
Rajendra et al: "The condensation of primary alcohols with resorcinol and other hydroxy aromatic compounds" Journal of the American Chemical Society, 1925, pp. 1079-1091, XP002534461.
Schiering et al., Crystal structure of the tyrosine kinase domain of the hepatocyte growth factor receptor c-Met and its complex with the microbial alkaloid K-252a Proceedings of the National Academy of Sciences USA 100: 12654-12659, Oct. 2003.
Shkil et al., "Recylization of Salts of Asymmetric Hantzcsh Pyridines," Chemistry of Heterocyclic Compounds, vol. 31, No. 1, 1995, pp. 76-79, XP002530500.
Veber et al., "Molecular properties that influence the oral bioavailability of drug candidates" Journal of Medicinal Chemistry 45: 2615-2623, Jun. 2002.
Wang et al., Potent and selective inhibitors of the Met [hepatocyte growth factor/scatter factor (HGF/SF) receptor] tyrosine kinase block HGF/SF-induced tumor cell growth and invasion Molecular Cancer Therapeutics 2: 1085-1092, Nov. 2003.
Würthner, F. et al., "Dimerization of Merocyanine Dyes. Structural and Energetic Characterization of Dipolar Dye Aggregates and Implications for Nonlinear Optical Materials" Am. Chem. Soc., 124: 9431-9447, 2002.
Würthner, F., "DMF in Acetic Anhydride: A Useful Reagent for Multiple-Component Syntheses of Merocyanine Dyes" Synthesis., 12: 2103-2113, 1999.
Ye et al: "Isolation of a fluorine pigment from the Indian paint fungus Echinodontium tinctorium and Pyrofomes albomarginatus" Tetrahedron, Elsevier Science Publishers, Amsterdam, NL, vol. 52, No. 16, Apr. 15, 1996, pp. 5793-5798, XP005922141.
Zou et al., An orally available small-molecule inhibitor of c-Met, PF-2341066, exhibits cytoreductive antitumor efficacy through antiproliferative and antiangiogenic mechanisms Cancer Research 67: 4408-4417, May 2007.

* cited by examiner

| Structure ID | 30267662 |
|---|---|
| CNC ID | 6017302 |
| Composition | C19H10Cl2O5 |
| Mass | 389.19455 |
| Chiral? | No |

COMPOSITIONS AND METHODS FOR INHIBITION OF HEPATOCYTE GROWTH FACTOR RECEPTOR C-MET SIGNALING

CROSS REFERENCE TO RELATED APPLICATIONS

This application is the National Stage filing of International Application No. PCT/US2009/038915, filed Mar. 31, 2009, which claims the benefit of U.S. Provisional Application No. 61/041,523, filed Apr. 1, 2008, the entireties of which are incorporated by reference herein.

STATEMENT REGARDING FEDERALLY SPONSORED RESEARCH OR DEVELOPMENT

This invention was made with Government support under grant number Z01 BC010639; grant number Z01 BC006198 and grant number Z01 SC006659. The United States Government has certain rights in the invention.

FIELD

This invention generally relates to derivatives and analogs of inhibitors of receptor tyrosine kinase c-Met, pharmaceutical compositions containing derivatives and analogs of c-Met inhibitors, methods of making derivatives and analogs of c-Met inhibitors and methods of use thereof.

BACKGROUND

Hepatocyte growth factor (HGF) is a secreted, heparin-binding protein that stimulates mitogenesis, motogenesis, and morphogenesis in a wide spectrum of cellular targets. Its receptor is the receptor tyrosine kinase (RTK) c-Met. Activation of the HGF/c-Met signaling pathway leads to a variety of cellular responses, including proliferation and survival, angiogenesis, and motility and invasion. Ma et al., *Cancer and Metastasis Reviews* 22: 309-325, 2003. Overexpression of c-Met and uncontrolled activation of its signaling pathway occurs in many human cancers. The presence of increased expression of either c-Met or HGF in tumor cell lines has been shown to correlate with tumor aggressiveness and decreased survival rates in several types of cancer. Wang et al., *Molecular Cancer Therapeutics* 2: 1085-1092, 2003.

The overall structure of the c-Met receptor (FIG. 1) is that of a typical RTK, with an extracellular ligand binding domain, a transmembrane helix, and an intracellular kinase domain. HGF binding to the extracellular domain promotes receptor dimerization and the autophosphorylation of several tyrosine residues in the kinase domain, leading to kinase activation. Ma et al., *Cancer and Metastasis Reviews* 22: 309-325, 2003. As shown in FIG. 1A, the intracellular domain has a typical kinase fold, with a β-sheet-containing lobe and a helical lobe connected through a hinge region. The ATP binding site (FIG. 1B), is in a deep, narrow, coin-slot-like cleft between the two lobes. Schiering et al., *Proceedings of the National Academy of Sciences USA* 100: 12654-12659, 2003. Germline and somatic missense mutations in the kinase domain of c-Met, leading to increased kinase activity, have been found in papillary renal cell carcinomas and in cancers of the lung, thyroid and head and neck. This suggests that selective inhibition of the kinase domain may be a viable therapeutic strategy for the treatment of papillary renal carcinoma and possibly several other human cancers. Most existing kinase domain inhibitors target the ATP binding site. It was originally thought that identifying inhibitors selective to only one kinase domain would be difficult, since there are many kinases, all of which bind ATP, and the sequence of residues in the ATP binding site is highly conserved. However, in contrast to this original belief, in recent years selective kinase inhibitors have been developed. Gould et al., *Pharmacology & Therapeutics* 93: 169-178, 2002; Noble et al., *Science* 303: 1800-1805, 2004; Bellon et al., *J. Biol. Chem.* 283: 2675-2683, 2008; Kim et al., Abstract MEDI-361 at 234th National American Chemical Society Meeting, Boston, Mass., Aug. 19-23, 2007. Despite the availability of selective kinase inhibitors, a need exists in the art for developing improved therapeutic compositions for treatment of cancer related to mutations in the c-Met kinase domain.

SUMMARY

This invention generally relates to derivatives and analogs of inhibitors of receptor tyrosine kinase c-Met, pharmaceutical compositions containing derivatives and analogs of c-Met inhibitors, methods of making derivatives and analogs of c-Met inhibitors and methods for treatment of neoplastic disease.

With respect to inhibitors of c-Met tyrosine kinase, "derivative" refers to a compound of the general Formula I:

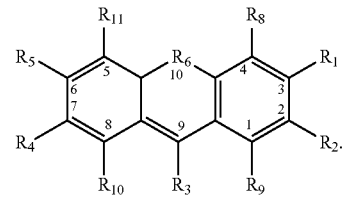

With reference to Formula I, or a pharmaceutically acceptable salt thereof, $R_1$, and $R_2$ can each independently be H, —CN, S, O, N, F, —CH$_2$—OH, —OH, $C_1$-$C_4$ alkyl, amine, or ethanone; wherein at least one of $R_1$ or $R_2$ is —CN, S, O, N, or F; $R_3$ can be H, lower alkyl; or phenyl optionally mono- or di-substituted with hydroxyl, alkoxy, alkyl, halo; or morpholinoalkyl; or phenylalkyl or naphthylalkyl, each optionally substituted with H, alkyl, halo, or haloalkyl; wherein alkyl is $C_1$-$C_4$ alkyl; $R_4$ and $R_5$ can each independently be H, —CN, S, O, N, F, OH, $C_1$-$C_4$ alkyl, phenyl, or morpholinoalkyl, wherein the phenyl groups are optionally substituted with one or more hydroxyl, alkyl, or halo groups and at least one of $R_4$ and $R_5$ is —CN, S, O, N, F, or OH; $R_6$ can be O or N—$R_7$; $R_7$ and $R_8$ can each independently be H; $C_1$-$C_4$ alkyl; hydroxyalkyl; carboxyalkyl; phenyl optionally substituted with one or more substituents selected from hydroxyl, alkoxy, carboxyl, halo, and acetamide-oxy; phenylamido; phenylamido carboxyl; phenylalkyl; phenylalkenyl; phenylhydrazonoalkyl; morpholinoalkyl; piperidine-proprionyl optionally substituted with carboxyl; or chromen-5-one optionally substituted with alkyl, dialkyl, or amino; and $R_9$, $R_{10}$, and $R_{11}$ can each independently be H, lower alkyl, or halo.

A method for treating neoplastic disease in a mammal believed to be responsive to treatment with a c-Met tyrosine kinase inhibitor is provided which comprises administering to the mammal a therapeutic amount of a compound of Formula I, wherein $R_1$ and $R_2$ are each independently H, —CN, S, O, N, F, —CH$_2$—OH, —OH, $C_1$-$C_4$ alkyl, amine, or ethanone, and at least one of $R_1$ and $R_2$ is —CN, S, O, N, or F.

$R_3$ is H; $C_1$-$C_4$ alkyl optionally substituted with halo or sulfonate; phenyl, phenoxy, or phenoxyalkyl, each optionally substituted with one or two substituents selected from hydroxyl, alkoxy, alkyl, halo, acetamido, acetamido alkoxy, carboxyl, and optionally-substituted amino; indolyl; pyridinyl; furanyl; thiophenyl; benzo[1,3]dioxolyl; or morpholinoalkyl, phenylalkyl or naphthylalkyl, each optionally substituted with alkyl, halo, or haloalkyl.

$R_4$ and $R_5$ are each independently H; —CN; S; O; N; F; OH; $C_1$-$C_4$ alkyl; amine; ethanone; phenyl optionally substituted with hydroxyl, alkyl, or halo; or morpholinoalkyl, and at least one of $R_4$ and $R_5$ is —CN, S, O, N, F, or OH.

$R_6$ is O or N—$R_7$.

$R_7$ and $R_8$ are each independently H; $C_1$-$C_4$ alkyl; hydroxyalkyl; carboxyalkyl; phenyl optionally substituted with one or more substituent selected from hydroxyl, alkoxy, carboxyl, halo, and acetamide-oxy; phenylamido; phenylamido carboxyl; phenylalkyl; phenylalkenyl; phenylhydrazonoalkyl; morpholinoalkyl; piperidine-proprionyl optionally substituted with carboxyl; or chromen-5-one optionally substituted with alkyl, dialkyl, or amino.

$R_9$, $R_{10}$, and $R_{11}$ are each independently H, lower alkyl, or halo.

A pharmaceutical composition is of Formula I is provided. In preferred embodiments of the invention, compounds of formula I, and compositions comprising the compounds, are provided in which $R_1$ is =O; $R_2$, $R_4$ and $R_5$ are OH; $R_3$ is phenyl di-substituted with chloro; $R_6$ is O; and $R_8$, $R_9$, $R_{10}$, and $R_{11}$ are each H. The compounds or pharmaceutical composition can be 9-(2,3-dichloro-phenyl)-2,6,7-trihydroxy-xanthen-3-one, or a pharmaceutically acceptable salt thereof.

BRIEF DESCRIPTION OF THE DRAWINGS

FIGS. 1A and 1B show the three-dimensional structure of the c-Met kinase domain and interactions with the crystal structure ligand, K252a.

DETAILED DESCRIPTION

Figure 1A:
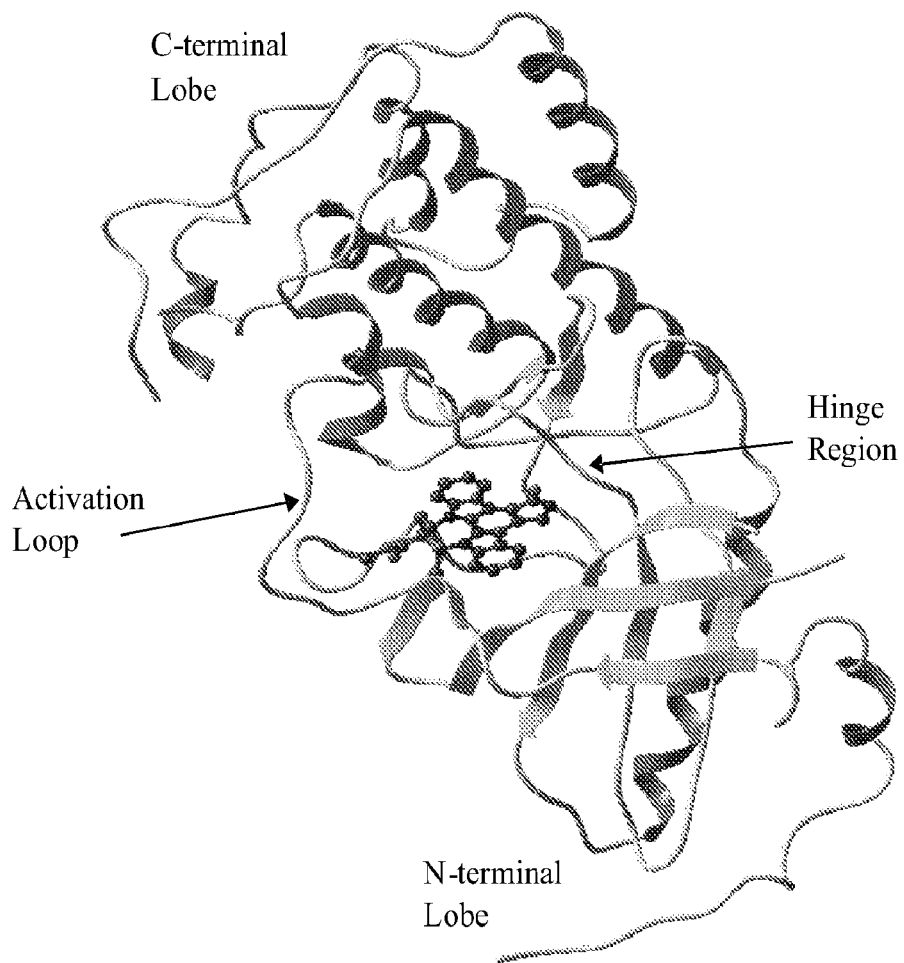

With respect to inhibitors of c-Met tyrosine kinase, "derivative" refers to a compound of the general Formula I:

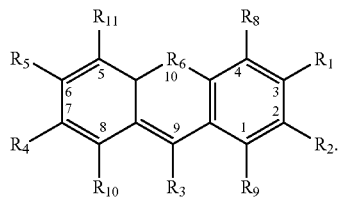

where the variables are as defined herein.

One method for achieving selectivity of kinase inhibitors is to target an inactive conformation of the binding site. Noble et al., *Science* 303: 1800-1805, 2004. This is a useful strategy for c-Met because in the crystal structure of c-Met complexed with the staurosporine analog, K-252a, the activation loop adopts a unique inhibitory conformation such that ATP and substrate peptides cannot bind. Schiering, et al., *Proc. Natl. Acad. Sci. USA*, 100: 12654-12659, 2003. To identify c-Met tyrosine kinase inhibitors useful as therapeutics for cancer treatment, a virtual screen was developed to identify new lead compounds that inhibit the c-Met kinase and specifically its conformation in the inactive state.

With respect to c-Met tyrosine kinase inhibitor, "analog" or "functional analog" refers to a modified form of the respective c-Met tyrosine kinase inhibitor in which one or more chemically derivatized functional side groups or linking groups ($R_1$, $R_2$, $R_3$, $R_4$, $R_5$, $R_6$, $R_7$, $R_8$, $R_9$, $R_{10}$, or $R_{11}$) has been modified such that the analog retains substantially the same biological activity or improved biological activity as the unmodified c-Met tyrosine kinase inhibitor in vivo and/or in vitro.

The present invention provides a virtual screen to identify new lead compounds that inhibit the c-Met kinase and specifically its conformation in the inactive state. The general objective of virtual screening is to select a small subset of compounds predicted to have activity against a given biological target out of a large database of available samples, either in-house compounds or purchasable chemicals. In "real" high-throughput screening, thousands to hundreds of thousands of compounds are screened in parallel. The goal of "virtual" high-throughput screening is to test compounds computationally in order to reduce the number of compounds that are tested experimentally. The number of compounds in the final set can be adjusted according to the resources available for assaying. A variety of computational methods can be used for virtual screening depending on the desired size of the final subset and on the amount of information known about the target, its natural ligands, and any known inhibitors. The screening methods provided herein included filtering of a large database of commercially available compounds based on physicochemical properties, receptor—ligand docking and scoring, and pharmacophore searches within the docking results. This produced an initial subset of approximately 600,000 compounds, which was reduced to a final set of 175 molecules. This set had very little structural similarity to known kinase inhibitors. The set was ranked using detailed forcefield calculations, and the top 70 compounds were purchased for testing in a cell-free system as well as in intact cells using an electrochemiluminescence assay of c-Met activation. Two of the compounds tested showed inhibition of c-Met at micromolar or submicromolar levels.

c-Met targeted drug development strategy to identify selective tyrosine kinase inhibitors was developed having three basic components: (1) a virtual screen of the 13.5 million compound ChemNavigator structure database using the c-Met crystal structure during the core docking step; (2) a biological screen of lead structures obtained in the virtual screen, using cell-free and intact cell-based assays; and (3) iterative refinement of biological leads through advanced virtual docking, rational design and chemical synthesis.

The virtual screen identified new lead compounds that inhibit the c-Met kinase specifically in its inactive conformation. Furthermore the biological screening of the 70 available compounds predicted to have activity by virtual screening is described. Two assays were developed to detect c-Met signaling inhibitors: an intact cells assay that provided information on receptor autophosphorylation state as well as cellular expression levels, and a second, cell-free assay, for identifying direct inhibitors of c-Met TK activation in vitro. Both assays utilize electrochemiluminescence detection technology; in contrast to conventional enzyme-linked detection methods, this technology uses antibodies (or other probes) tagged with Ruthenium. Ruthenium tagged antibody binding is then detected by light emission, which occurs when voltage is applied in the presence of specific redox reagents. Emitted light is measured digitally using a cooled CCD camera, permitting significantly improved sensitivity and linear dynamic range relative to more conventional methods. Results from the assay were normalized to standard curves prepared using recombinantly expressed, purified c-Met protein to maximize reproducibility and to provide absolute values of cellular receptor content and kinase inhibition.

Two classes of c-Met-active compounds were identified with micromolar 1050 values. One compound class acted through both c-Met protein down-regulation (detected using an intact cell screen) and TK inhibition, while the other exhibited classic TK inhibition through competitive ATP binding antagonism (detected using a cell-free kinase assay). Lead compounds from this step were further analyzed in silico and new structures were rationally designed for improved c-Met interaction, yielding second generation structures with improved potency.

Hepatocyte growth factor (HGF) is an important regulator of normal development and homeostasis, and dysregulated signaling through the HGF receptor, c-Met, contributes to tumorigenesis, tumor progression and metastasis in numerous human malignancies. The development of selective small-molecule inhibitors of oncogenic tyrosine kinases (TK) has led to well-tolerated, targeted therapies for a growing number of cancer types. The subsequent biological screening of in silico lead structures using cell-free and intact cell assays is described. Lead compounds from this step were further analyzed in silico and new structures were rationally designed for improved c-Met interaction, yielding second generation structures with improved potency.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" or "an agonist" includes a plurality of such antagonists or a plurality of such agonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "µM" means micromolar, "mM" means millimolar, "M" means molar, "mmole" means millimole(s), "cm" means centimeters, "SEM" means standard error of the mean and "IU" means International Units, "IC50" means 50% maximum inhibitory concentration (micromoles/L); "° C." means degrees Celsius. "$\Delta ED_{50}$ value" means dose which results in 50% alleviation of the observed condition or effect (50% mean maximum endpoint), "$\Delta ID_{50}$" means dose which results in 50% inhibition of an observed condition or effect or biochemical process (50% mean maximum endpoint).

"Antagonist" or "c-Met tyrosine kinase antagonist" refers to an endogenous or exogenous compound, substance or entity that opposes the physiological effects of another compound and, at the receptor level, it is an endogenous or exogenous compound, substance or entity that has affinity for and opposes and/or blocks at least one of the normal physiological responses normal induced by another compound, substance or entity at the cell receptors. As used herein, the term refers to a c-Met tyrosine kinase inhibitor derivative or analog, a suitable homolog, or a portion thereof, which blocks at least one of the normal actions of c-Met tyrosine kinase. For example, treatment with certain c-Met tyrosine kinase antagonists can be used to treat neoplastic disease in a mammalian subject.

"Receptor" refers to a molecule, a polymeric structure, or polypeptide in or on a cell that specifically recognizes and binds a compound acting as a molecular messenger, for example, neurotransmitter, hormone, lymphokine, lectin, or drug.

"Lower alkyl" refers to an optionally substituted, saturated straight or hydrocarbon having from about 1 to about 12 carbon atoms (and all combinations and subcombinations of ranges and specific numbers of carbon atoms therein), with from about 1 to about 8 carbon atoms, being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, 3-methylpentyl, 2,2-dimethylbutyl, and 2,3-dimethylbutyl. Specifically included within the definition of "lower alkyl" are those aliphatic hydrocarbon chains that are optionally substituted.

"Cyclic alkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred. Multi-ring structures can be bridged or fused ring structures. Groups include, but are not limited to, cyclopropyl, cyclobutyl, cyclopentyl, cyclohexyl, cyclooctyl, and adamantyl. Specifically included within the definition of "cyclic alkyl" are those aliphatic hydrocarbon chains that are optionally substituted.

"Perfluorinated alkyl" refers to an alkyl, as defined above, in which the hydrogens directly attached to the carbon atoms are completely replaced by fluorine.

"Alkenyl" refers to an alkyl group of at least two carbon atoms having one or more double bonds, wherein alkyl is as defined herein. Alkenyl groups can be optionally substituted.

"Alkynyl" refers to an alkyl group of at least two carbon atoms having one or more triple bonds, wherein alkyl is as defined herein. Alkynyl groups can be optionally substituted.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring" refers to a stable 5- to 7-membered monocyclic or bicyclic ring, a 7- to 10-membered bicyclic heterocyclic ring, or a 12- to 15-membered tricyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

"Alkoxy" refers to the group R—O— where R is an alkyl group as defined herein.

"Aryloxy" refers to the group R—O— where R is an aryl group, as defined herein.

"Heteroaryloxy" refers to the group R—O— where R is a heteroaryl group, as defined herein.

"Alkanoyl" refers to the group R—C(═O) where R is an alkyl group of 1 to 5 carbon atoms.

"Alkanoyloxy" refers to the group R—C(═O)—O where R is an alkyl group of 1 to carbon atoms.

"Halo," refers to chloro, bromo, fluoro, and iodo.

"Haloalkyl," or "haloaryl" refers to an alkyl or aryl, as defined above, in which one or more hydrogens directly attached to the carbon atoms are replaced by one or more halo substituents.

"Optional" or "optionally" means that the subsequently described event or circumstance may or may not occur, and that the description includes instances in which it does not.

For example, optionally substituted phenyl indicates either unsubstituted phenyl, or phenyl mono-,di-, or tri-substituted, independently, with OH, COOH, lower alkyl, lower alkoxy, halo, nitro, amino, alkylamino, dialkylamino, trifluoromethyl and/or cyano.

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (Vols. 1-3, 1992); Lloyd, 1999, *The Art, Science And Technology Of Pharmaceutical Compounding*; and Pickar, 1999, Dosage Calculations).

"Effective amount" refers to an amount of a compound that can be therapeutically effective to inhibit, prevent or treat the symptoms of particular disease, disorder or side effect.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Stereoisomer, prodrug, pharmaceutically acceptable salt, hydrate, solvate, acid salt hydrate, N-oxide or isomorphic crystalline form thereof" refer to derivatives of the disclosed compounds wherein the parent compound is modified by making acid or base salts thereof. Examples of stereoisomer, prodrug, pharmaceutically acceptable salt, hydrate, solvate, acid salt hydrate, N-oxide or isomorphic crystalline form thereof include, but are not limited to, mineral or organic acid salts of basic residues such as amines; alkali or organic salts of acidic residues such as carboxylic acids; and the like. The stereoisomer, prodrug, pharmaceutically acceptable salt, hydrate, solvate, acid salt hydrate, N-oxide or isomorphic crystalline form thereof include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present compositions and methods.

Certain acidic or basic compounds can exist as zwitterions. All forms of the compounds, including free acid, free base and zwitterions, are contemplated to be within the scope of the present compositions and methods. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

"Treating" or "treatment includes the administration of the compounds or agents of the present invention to prevent or delay the onset of the symptoms, complications, or biochemical indicia of a disease, alleviating the symptoms or arresting or inhibiting further development of the disease, condition, or disorder (e.g., cancer). Treatment may be prophylactic (to prevent or delay the onset of the disease, or to prevent the manifestation of clinical or subclinical symptoms thereof) or therapeutic suppression or alleviation of symptoms after the manifestation of the disease. Treatment is understood to include the administration of the c-Met tyrosine kinase inhibitor or derivative thereof in a manner where the measure of effectiveness of the treatment can be measured as, for example, disease-free progression, progression-free survival, and overall survival or other measures of drug effectiveness which are used as endpoints or surrogate endpoints in clinical trials regulated by the U.S. Food and Drug Administration (FDA) or similar regulatory authorities, e.g., the European Medicines Agency (EMEA).

In general, the phrase "well tolerated" refers to the absence of adverse changes in health status that occur as a result of the treatment and would affect treatment decisions.

Except when noted, the terms "patient" or "subject" are used interchangeably and refer to mammals such as human patients and non-human primates, as well as experimental animals such as rabbits, rats, and mice, and other animals.

"Prodrug" refers to compounds specifically designed to maximize the amount of active species that reaches the desired site of reaction which are of themselves typically inactive or minimally active for the activity desired, but through biotransformation are converted into biologically active metabolites.

"Stereoisomers" refers to compounds that have identical chemical constitution, but differ as regards the arrangement of the atoms or groups in space.

When any variable occurs more than one time in any constituent or in any formula, its definition in each occurrence is independent of its definition at every other occurrence. Combinations of substituents and/or variables are permissible only if such combinations result in stable compounds.

Pharmaceutical Compositions c-Met tyrosine kinase inhibitor derivatives and analogs useful in the present compositions and methods can be administered to a human patient per se, in the form of a stereoisomer, prodrug, pharmaceutically acceptable salt, hydrate, solvate, acid salt hydrate, N-oxide or isomorphic crystalline form thereof, or in the form of a pharmaceutical composition where the compound is mixed with suitable carriers or excipient(s) in a therapeutically effective amount, for example, to treat neoplastic disease.

Routes of Administration

The c-Met tyrosine kinase inhibitor derivatives and analogs and pharmaceutical compositions described herein can be administered by a variety of routes. Suitable routes of administration can, for example, include oral, rectal, transmucosal, or intestinal administration; parenteral delivery, including intramuscular, subcutaneous, intramedullary injections, as well as intrathecal, direct intraventricular, intravenous, intraperitoneal, spinal, epidural, intranasal, or intraocular injections. Alternatively, one can administer the compound in a local rather than systemic manner, for example via injection of the compound directly into the subject, often in a depot or sustained release formulation. Furthermore, one can administer the compound in a targeted drug delivery system, for example, in a liposome coated vesicle. The liposomes can be targeted to and taken up selectively by the tissue of choice. In a further embodiment, the c-Met tyrosine kinase inhibitor derivatives and analogs and pharmaceutical compositions described herein are administered orally.

Composition/Formulation

The pharmaceutical compositions described herein can be manufactured in a manner that is itself known, e.g., by means of conventional mixing, dissolving, granulating, dragee-making, levigating, emulsifying, encapsulating, entrapping or lyophilizing processes. Pharmaceutical compositions for use as described herein can be formulated in conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents can be formulated in aqueous solutions, e.g., in physiologically compatible buffers such as Hanks' solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner. For administration by inhalation, the compounds for use are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides. In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A suitable pharmaceutical carrier for hydrophobic compounds is a cosolvent system comprising benzyl alcohol, a nonpolar surfactant, a water-miscible organic polymer, and an aqueous phase. The cosolvent system can be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose. Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity.

Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few weeks up to over 100 days. The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutically acceptable carriers are determined in part by the particular composition being administered, as well as by the particular method used to administer the composition. Accordingly, there is a wide variety of suitable formulations of pharmaceutical compositions for administering the c-Met tyrosine kinase inhibitor compounds (see, e.g., *Remington's Pharmaceutical Sciences*, Mack Publishing Co., Easton, Pa. $18^{th}$ ed., 1990, incorporated herein by reference). The pharmaceutical compositions generally comprise a differentially expressed protein, agonist or antagonist in a form suitable for administration to a patient. The pharmaceutical compositions are generally formulated as sterile, substantially isotonic and in full compliance with all Good Manufacturing Practice (GMP) regulations of the U.S. Food and Drug Administration.

Effective Dosages

Pharmaceutical compositions suitable for use include compositions wherein the c-Met tyrosine kinase inhibitor derivatives and analogs are contained in a therapeutically effective amount. Determination of an effective amount is well within the capability of those skilled in the art, especially in light of the detailed disclosure provided herein. For any compound used in the present method, a therapeutically effective dose can be estimated initially from cell culture assays. For example, a dose can be formulated in animal models to achieve a circulating concentration range that includes the $I_{50}$ as determined in cell culture (i.e., the concentration of test compound that is lethal to 50% of a cell culture) or the $I_{100}$ as determined in cell culture (i.e., the concentration of compound that is lethal to 100% of a cell culture). Such information can be used to more accurately determine useful doses in humans. Initial dosages can also be formulated by comparing the effectiveness of the c-Met tyrosine kinase inhibitor derivatives and analogs described herein in cell culture assays with the effectiveness of known cancer medications. In this method an initial dosage can be obtained by multiplying the ratio of effective concentrations obtained in cell culture assay for the c-Met tyrosine kinase inhibitor derivatives and analogs and a known cancer drug by the effective dosage of the known cancer drug. For example, if an c-Met tyrosine kinase inhibitor derivative or analog is twice as effective in cell culture assay than the cancer drug (i.e., the $I_{50}$ c-Met tyrosine kinase inhibitor is equal to one half times the $I_{50}$ cancer drug in the same assay), an initial effective dosage of the c-Met tyrosine kinase inhibitor derivative or analog would be one-half the known dosage for the cancer drug. Using these initial guidelines one having ordinary skill in the art could determine an effective dosage in humans. Initial dosages can also be estimated from in vivo data. One having ordinary skill in the art could readily optimize administration to humans based on this data. Dosage amount and interval can be adjusted individually to provide plasma levels of the active compound which are sufficient to maintain therapeutic effect. Usual patient dosages for oral administration range from about 50-2000 mg/kg/day, typically from about 250-1000 mg/kg/day, from about 500-700 mg/kg/day or from about 350-550 mg/kg/day. Therapeutically effective serum levels will be achieved by administering multiple doses each day. In cases of local administration or selective uptake, the effective local concentration of the drug can not be related to plasma concentration. One having skill in the art will be able to optimize therapeutically effective local dosages without undue experimentation. The amount of composition administered will, of course, be dependent on the subject being treated, on the subject's weight, the severity of the affliction, the manner of administration and the judgment of the prescribing physician. The therapy can be repeated intermittently while neoplastic disease is detectable or even when they are not detectable. Moreover, due to its apparent nontoxicity, the therapy can be provided alone or in combination with other drugs, such as for example, anti-inflammatories, antibiotics, corticosteroids, vitamins and the like. Possible synergism between the c-Met tyrosine kinase inhibitor derivatives or analogs described herein and other drugs can occur. In addition, possible synergism between a plurality of c-Met tyrosine kinase inhibitor derivatives or analogs can occur.

The typical daily dose of a pharmaceutical composition of c-Met tyrosine kinase inhibitor derivatives and analogs varies according to individual needs, the condition to be treated and with the route of administration. Suitable doses are in the general range of from 0.001 to 10 mg/kg bodyweight of the recipient per day. Within this general dosage range, doses can be chosen at which the pharmaceutical composition of c-Met tyrosine kinase inhibitor derivatives and analogs has an effect to reduce or eliminate neoplastic disease. In general, but not exclusively, such doses will be in the range of from 0.5 to 10 mg/kg.

In addition, within the general dose range, doses can be chosen at which the compounds pharmaceutical composition of c-Met tyrosine kinase inhibitor derivatives and analogs has an effect to reduce or eliminate neoplastic disease. In general, but not exclusively, such doses will be in the range of from 0.001 to 0.5 mg/kg. It is to be understood that the 2 sub ranges noted above are not mutually exclusive and that the particular activity encountered at a particular dose will depend on the nature of the pharmaceutical composition of c-Met tyrosine kinase inhibitor derivatives and analogs used.

The pharmaceutical composition of c-Met tyrosine kinase inhibitor derivatives and analogs can be in unit dosage form, for example, a tablet or a capsule so that the patient can self-administer a single dose. In general, unit doses contain in the range of from 0.05-100 mg of a compound of the pharmaceutical composition of c-Met tyrosine kinase inhibitor derivatives and analogs. Unit doses contain from 0.05 to 10 mg of the pharmaceutical composition. The active ingredient can be administered from 1 to 6 times a day. Thus daily doses are in general in the range of from 0.05 to 600 mg per day. In an embodiment, daily doses are in the range of from 0.05 to 100 mg per day or from 0.05 to 5 mg per day.

Toxicity

Toxicity and therapeutic efficacy of the c-Met tyrosine kinase inhibitor derivatives and analogs described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$ Compounds which exhibit high therapeutic indices are chosen. The data obtained from these cell culture assays and animal studies can be used in formulating a dosage range that is not toxic for use in human. The dosage of such compounds lies within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1). One of the advantages, among others, of using the c-Met tyrosine kinase inhibitor derivatives and analogs described herein to treat neoplastic disease is their lack of toxicity. For example, it has been found that repeated intraperitoneal doses of 75 mg/kg produced no ill effects in mice (see Example 5). Since the i.v. serum half-life ($t_{1/2}$) of $T_1$ amine is about 2-2.5 hours, repeated daily dosages of the c-Met tyrosine kinase inhibitor described herein without ill effects is predictable.

Other embodiments and uses will be apparent to one skilled in the art in light of the present disclosures.

The invention will be further described with reference to the following examples; however, it is to be understood that the invention is not limited to such examples.

Example 1

Virtual Screening

Methods

Preliminary Database Processing. The August 2004 release plus the November 2004 update of the ChemNavigator iResearch Library was processed using the chemoinformatics toolkit CACTVS to add explicit hydrogens to the chemical structures, to standardize the encoding of certain functional groups, and to generate three-dimensional coordinates with CORINA. Ihlenfeldt et al., *Journal of Chemical Information and Computer Sciences* 34: 109-116, 1994; Gasteiger et al., *Tetrahedron Computer Methodology* 3: 547-547, 1990. In preliminary filtering using the program Pipeline Pilot (*Pipeline Pilot*; version 4.1.1; SciTegic, Inc.: San Diego, Calif.), we removed any salts and solvents, keeping only the largest fragment in each molecular record, and filtered out compounds containing atoms other than H, C, N, O, P, S, F, Cl, Br, and I; compounds with a molecular weight less than 100 or greater than 800; compounds with more than 15 rotatable bonds (excluding terminal rotors); compounds with a logP of less than −3.0 or greater than 8.0; and compounds with more than one undefined stereocenter. We then eliminated any duplicate structures.

Preparation of Crystal Structure. We began with the crystal structure (1R0P in the PDB) of the kinase domain of c-Met crystallized with the inhibitor K-252a, a staurosporine analog. Schiering et al., *Proceedings of the National Academy of Sciences USA* 100: 12654-12659, 2003. We prepared the structure for docking by deleting the crystal waters, capping the terminal and loop ends (where regions of the sequence were disordered in the crystal) with $NH_3^+$ or $COO^-$ groups, and adding explicit hydrogens. We defined the binding site as a sphere with radius 10 Å, centered at the midpoint of the bond between atoms C3 and C4 in K-252a.

Validation of Docking Protocol. We first constructed a small database of four known c-Met inhibitors along with K-252a and staurosporine to be used as a test case to determine optimal docking parameters. Wang et al., *Molecular Cancer Therapeutics* 2: 1085-1092, 2003; Christensen et al., *Cancer Research* 63: 7345-7355, 2003; Moriotti et al., *Oncogene* 21: 4885-4893, 2002. As discussed above, these inhibitors do not fit in the 1R0P crystal structure binding site, so a second small database composed of a series of 40 known kinase inhibitors with a variety of core structures from the literature was also constructed. Noble et al., *Science* 303: 1800-1805, 2004; Garcia-Echeverria et al., *Medicinal Research Reviews* 20: 28-57, 2000. We set up two GOLD docking runs to compare the GoldScore fitness function to the ChemScore fitness function. Jones et al., *Journal of Molecular Biology* 267: 727-748, 1997. We had found with previous work that the "library screening" genetic algorithm settings performed poorly, so we used the "7-8 times speedup" settings, and analyzed the docking results to choose a scoring function and a reasonable score cutoff value. There are no Ki or binding affinity data for this set of kinase inhibitors against c-Met, so we were unable to compare the scores from the two different scoring functions to experimental data. However, we found that ChemScore seemed to work well for generating reasonable poses, consistent with experimentally determined binding modes of the known inhibitors, but the value of the score itself had absolutely no predictive ability to distinguish between high- and low-affinity compounds. The GoldScore scoring function did not generate good poses, so we decided to use ChemScore with a generous score cutoff for keeping poses (since a low score did not necessarily mean that a pose was bad in this case).

c-Met-Specific Filtering of Processed ChemNavigator Database. Our test database of kinase inhibitors was also used to look for reasonable ranges for logP, polar surface area, molecular weight and other properties for filtering potential new inhibitors. We calculated a set of 32 properties for the known inhibitors using MOE, including several versions of logP, logD and solubility, and various estimations of polar/non-polar surface area. *MOE: Molecular Operating Environment*; version 2004.03. Chemical Computing Group, Inc.: Montreal, Canada. and Pipeline Pilot, *Pipeline Pilot*; version 4.1.1; SciTegic, Inc.: San Diego, Calif. Based on these results, we filtered the processed ChemNavigator database to keep only compounds with molecular weight between 250 and 500, more than 2 aromatic rings, fewer than 4 rotatable bonds (not counting terminal rotors), between 2 and 5 hydrogen bond acceptors, between 1 and 3 hydrogen bond donors, a logP value between 1.0 and 6.0, no phosphate or sulfate groups, a polar surface area less than 100 Å2, and a nonpolar surface area of at least 200 Å2.

Docking. Docking runs were performed using the program GOLD with the "7-8 times speedup" genetic algorithm settings, and the ChemScore fitness function. Wang et al., *Molecular Cancer Therapeutics* 2: 1085-1092, 2003, *MOE: Molecular Operating Environment*; version 2004.03; Chemical Computing Group, Inc.: Montreal, Canada. The "flip ring corners," "flip planar N," and "internal H-bonds" flags were set. Early termination was allowed if the top 5 solutions were within 1.5 Å RMSD. The ten highest-scoring poses were saved for each compound, and poses with ChemScore fitness less than 20.0 were rejected. The results and scores were saved in a single SD file for each run.

Pharmacophore-based Filtering. We set up a series of four receptor-based pharmacophore filters in MOE by defining required hydrogen bond or hydrophobic features for ligands based on the positions of atoms in the binding site. *MOE: Molecular Operating Environment*; version 2004.03; Chemical Computing Group, Inc.: Montreal, Canada. The first filter eliminated all poses that did not have a hydrogen bond to the backbone of hinge residues Pro 1158 or Met 1160; the second filter eliminated all poses that did not have a hydrophobic or aromatic interaction with the central hydrophobic residues Ile 1084, Val 1092, Met 1211, and Met 1229; the third filter defined a point at the centroid of Val 1092 CG1, Ala 1108 CB, and Leu 1157 CD1, and a second point at the centroid of Phe 1089 CE2 and CZ, and Lys 1110 CG, CD and CE and eliminated all poses that did not have a hydrophobic or aromatic atom within 2.5 Å of at least one of these points; and the fourth filter eliminated all poses that did not have either a hydrogen bond to Tyr 1230 N or an aromatic-aromatic interaction with the tyrosine ring. A successfully docked molecule must have passed all four filters. The SD file of docked poses was imported into a MOE database, and each pose was annotated with the PCH pharmacophore scheme. The database was then searched using each query with the "use absolute positions" option to test each pose in the frame of reference of the binding site, as it was docked by the docking program, rather than rotating each molecule to best match the query.

Ranking Commercially Available Hit Compounds. We used the previously-calculated set of physicochemical properties (molecular weight, number of hydrogen bond acceptors and donors, logP, polar surface area, and number of rotatable bonds) to establish that all the compounds followed Lipinski's rule of 58 and Veber's rules for oral bioavailability, with the exception of a few where logP was slightly high. Veber's work suggests that polar surface area is a better prediction of membrane permeability than logP, so these compounds were not eliminated from consideration. To evaluate binding site interactions we minimized each docked ligand in the binding site and calculated the force field interaction energy between protein and ligand, using eMBrAcE in MacroModel. Mohamadi et al., *Journal of Computational Chemistry* 11: 440-467, 1990. The energy minimization used the Polak-Ribiere conjugate gradient method, with convergence set to a gradient of 0.05, and the OPLS-AA forcefield with implicit GB/SA water solvent and extended non-bonded cutoffs. Residues I1084, G1085, F1089, V1092, K1110, L1157, P1158, Y1159, M1160, G1163, M1211, M1229, and Y1230 were allowed to move and a shell of residues within 5 Å of these was restrained with a force constant of 100 kcal/mol; all other residues were frozen. The compounds were then sorted according to the total interaction energy—the sum of the van der Waals, electrostatic, and solvation energies.

Results

Figure 2:
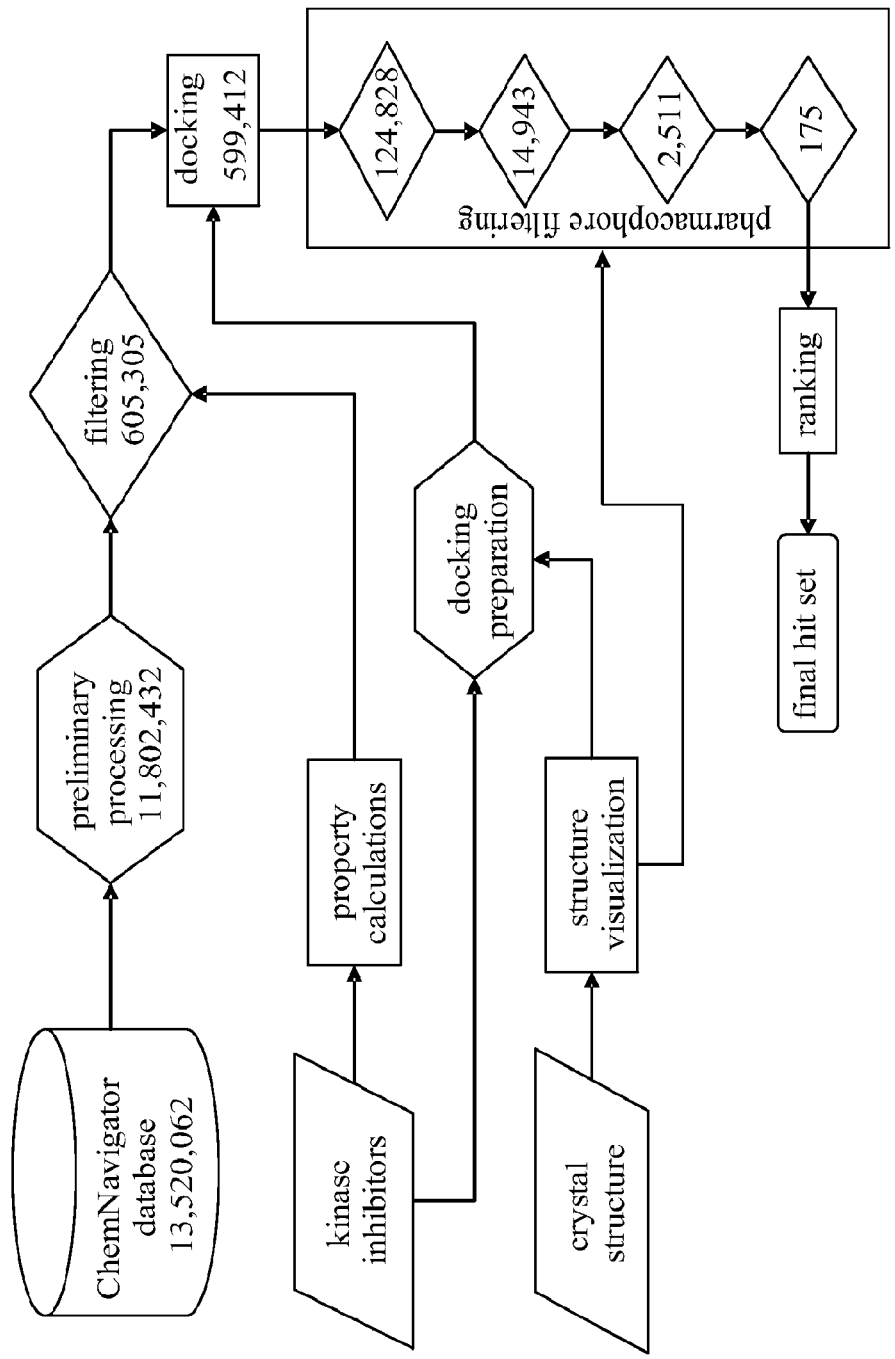
FIG. 2 shows a flowchart illustrating the virtual screening procedure.

A summary of the overall virtual screening procedure is given in FIG. 2. The November 2004 release of the Chem-Navigator database was used. The database is a compilation of commercially available chemical samples from 154 international chemistry suppliers. In the preliminary processing of the database, we added explicit hydrogens and calculated three-dimensional coordinates for each molecule. We also performed a first-stage processing in which we removed unsuitable and undesirable compounds: very large and very small molecules, inorganic compounds, molecules whose lipophilicity is too high or too low; molecules with more than 15 rotatable bonds which will not be handled well by the docking program, and molecules with more than one undefined stereocenter whose three-dimensional structures are therefore partially unknown. We further filtered the processed database to choose compounds whose physicochemical properties were within the ranges seen with known kinase inhibitors, indicating that the compounds were reasonable as new potential inhibitors of c-Met. Our filtering criteria included molecular weight, number of aromatic rings and rotatable bonds, polar and non-polar surface area, logP, and number of hydrogen bond donors and acceptors.

The target crystal structure (1R0P in the PDB) is of the kinase domain of c-Met crystallized with the inhibitor K-252a, a staurosporine analog. Schiering et al., *Proceedings of the National Academy of Sciences USA* 100: 12654-12659, 2003. We prepared the structure for docking and performed a test docking run with a series of 40 known kinase inhibitors with a variety of core structures from the literature. Noble et al., *Science* 303: 1800-1805, 2004. García-Echeverria et al., *Medicinal Research Reviews* 20: 28-57, 2000. We then docked the filtered database using GOLD, saving up to ten poses for each compound. Jones et al., *Journal of Molecular Biology* 267: 727-748, 1997. The majority of the compounds from the filtering in the previous step were docked successfully. This was desired because the docking program's scoring function had very little predictive ability to discern binders from non-binders.

We used the structural interactions between c-Met and those ligands that fit the binding site for analysis of the docked poses with pharmacophore-based filtering. This is not a step that is typically part of virtual screening; generally the process moves directly from docking to scoring, as a score for each docked pose is the output from the docking program. However, we have found that inserting a step, and filtering the docked poses with a series of pharmacophore queries to remove poses that do not form certain essential interactions with the target binding site, improves the quality of the results. This is because while existing scoring functions are generally good at producing reasonable docked poses of a molecule in a binding site, they are not necessarily good at discriminating between good binders and poor binders.

Figure 3:
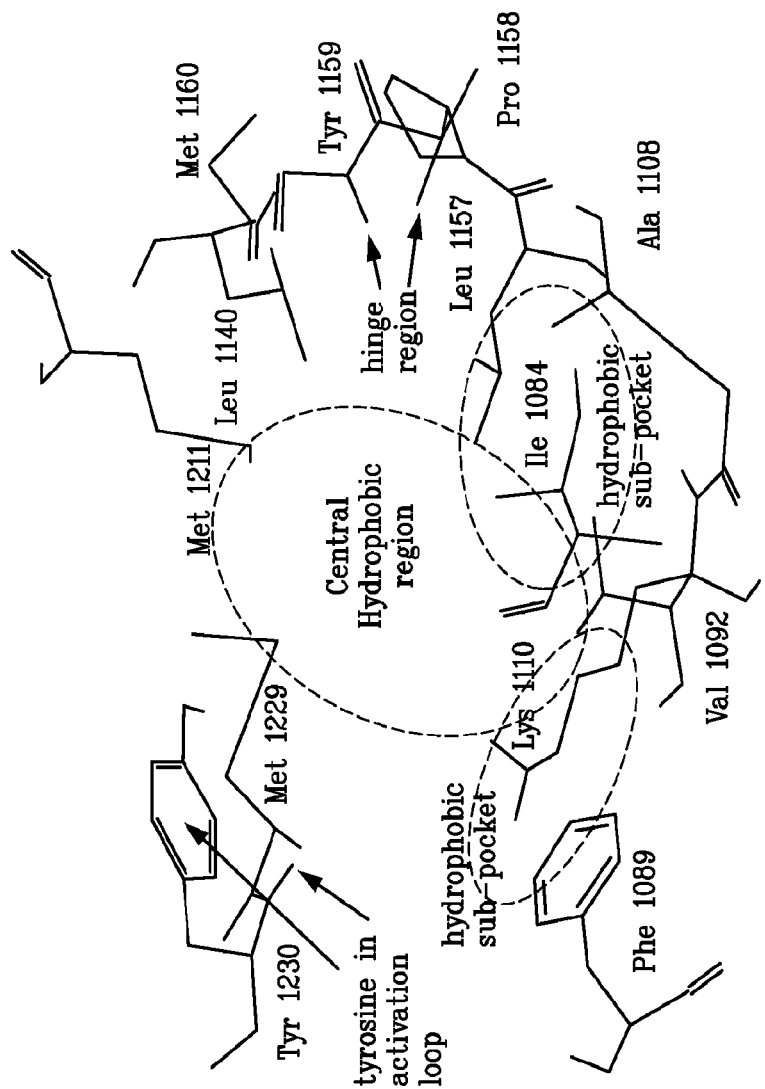
FIG. 3 illustrates the topographical features of the c-Met ATP binding site used to filter docked poses.

We filtered the docking results to enforce the presence of the following four interactions, illustrated in FIG. 3: 1) a hydrogen bond to residues in the hinge region, an interaction that is highly characteristic of all compounds bound to the ATP binding site in kinase domains; 2) a hydrophobic or aromatic interaction to fill up the central region of the pocket; 3) an additional hydrophobic or aromatic interaction in one of two smaller sub-pockets; and 4) either a hydrogen bond to Tyr 1230 N or an aromatic-aromatic interaction with the tyrosine ring. The hydrogen bonding between this tyrosine and the inhibitor K-252a seen in the crystal structure (FIG. 1B) suggests that an interaction with Tyr 1230 may be the key to inducing and stabilizing the inhibitory conformation of the activation loop. Schiering, et al., *Proc. Natl. Acad. Sci. USA,* 100: 12654-12659, 2003. The docked molecules that satisfied all four interaction criteria gave our final set of 175 compounds.

Figure 1B:
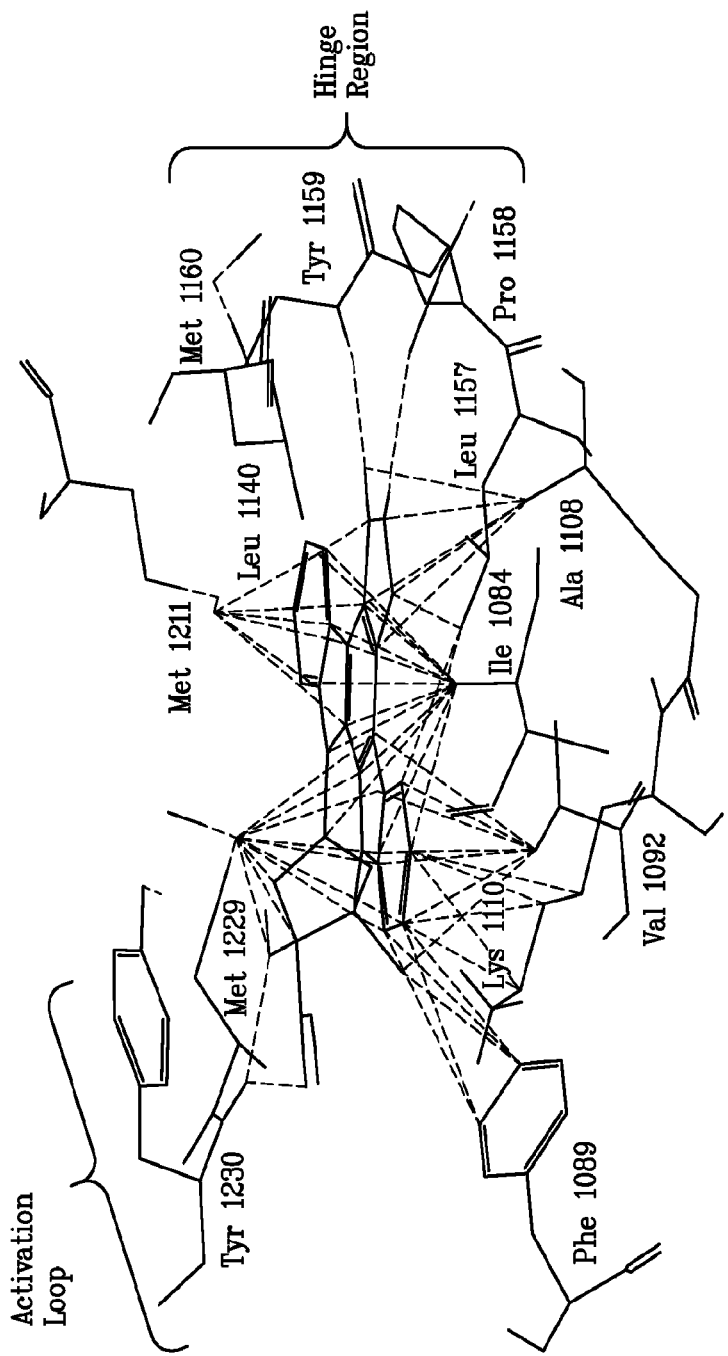

FIG. 1 shows A) The three-dimensional structure of the c-Met kinase domain. B) The hydrogen-bonding (dashed yellow lines) and hydrophobic (dashed green lines) residue interactions with the crystal structure ligand, K252a.

FIG. 2 shows a flowchart illustrating the virtual screening procedure and listing the number of compounds at each stage, from the starting point of a large database of small molecules along with a crystal structure and a set of known inhibitors, to the end point of a small set of compounds proposed for biological screening.

FIG. 3 illustrates the topographical features of the c-Met ATP binding site used to filter docked poses. An interaction with each region of the binding site was required for a successfully docked compound.

We then looked for any overlap between the final set and a database of 170,000 known kinase inhibitors (Kinase ChemBioBase from Jubilant Biosys). A search in this database for compounds with a Tanimoto similarity >0.6 to molecules in the final set found only 16 molecules in the final set with some substructural similarity to known inhibitors. We also calculated a series of physicochemical properties for the final set of compounds: molecular weight, number of hydrogen bond acceptors and donors, logP, polar surface area, and number of rotatable bonds, to establish that all the compounds follow Lipinski's Rule of Five and Veber's rules for oral bioavailability with the exception of a few where logP is slightly high. Lipinski et al., *Advanced Drug Delivery Reviews* 23: 3-25, 1997; Veber et al., *Journal of Medicinal Chemistry* 45: 2615-2623, 2002.

Out of the 175 molecules in the final set, 70 were available for purchase. The available compounds were also ranked for priority of testing according to the predicted strength of their interactions with binding site, using eMBrAcE in MacroModel. Mohamadi et al., *Journal of Computational Chemistry* 11: 440-467, 1990. Each docked ligand was energy minimized in the binding site and the total forcefield interaction energy (the sum of the van der Waals, electrostatic, and solvation energies) was calculated.

Example 2

Leads Obtained from Biological Cell-Free Screening

A cell-free assay was developed to measure c-Met TK activation (autophosphorylation) as a basis for identifying inhibitors of c-Met TK activation. The assay utilized a state-of-the-art detection technology called electrochemilumescence. In contrast to conventional enzyme-linked detection methods (e.g. ELISA), electrochemiluminescent technology uses antibodies (or other probes) tagged with Ruthenium. Ruthenium tagged antibody binding is then detected by light emission, which occurs when voltage is applied in the presence of specific redox reagents. Emitted light is measured digitally using a cooled CCD camera, yielding dramatic improvements in assay sensitivity and linear dynamic range when compared to conventional methods. Results from the assay were normalized to standard curves prepared using recombinantly expressed, purified control proteins to maximize reproducibility and to provide absolute values of kinase inhibition.

Cell-free Screen for c-Met Kinase Activity. Intact cultured cells were serum deprived for 24 to 48 h to obtain quiescent, unstimulated c-Met RTK. Cells were then rinsed briefly with PBS before lysis and protein extraction on ice with a buffer containing non-ionic detergent, protease and phosphatase inhibitors. Protein extracts were clarified by centrifugation, protein concentration was determined, and known quantities were then applied to streptavidin coated multiwell plates containing an immobilized biotinylated antibody specific for the c-Met ectodomain. Test compounds at various concentrations were incubated with unstimulated, immobilized c-Met in Kinase Buffer containing Triton X-100 (0.1%), 50 mM HEPES, pH 7.4, 5 mM $MgCl_2$, 5 mM $MnCl_2$, 20 µM ATP and protease inhibitors for 1 h at room temperature. Replicates (3 to 5) were used for every assay condition. In each assay, a previously characterized c-Met ATP binding antagonist (PHA665752, Tocris Biochemicals; or SU11274, NCI) was used as a positive control, and wells containing c-Met incubated in Kinase Buffer without ATP were used as a negative control. Vehicle controls were included as needed, typically at the concentration present in the highest compound concentration tested. The kinase reaction was terminated by rinsing with a Stop Buffer containing 50 mM HEPES, pH 7.4, 0.1% Triton X-100, 4 mM EDTA and phosphatase inhibitors. c-Met receptor content and autophosphorylation were measured as described above for intact cell assays; c-Met signals were converted to absolute amounts using a standard curve as also as described above.

Calculations and Statistical Analysis All biological samples were measured in duplicate unless otherwise noted; all electrochemiluminescence assay samples were performed in triplicate unless otherwise noted. Mean values from negative control (empty) wells were subtracted from all other raw values. A standard curve of c-Met protein concentration was constructed by plotting signal intensity against a purified recombinant c-Met protein standard. Nonlinear regression curve fitting algorithms (Microsoft Excel or GraphPad Prism software) were used to generate an equation from which sample values for c-Met concentration were derived from mean signal intensity values. Phospho-c-Met intensity measurements were normalized to c-Met intensity measurements to obtain phospho-c-Met/c-Met protein ratio. Mean values among groups were compared for statistically significant differences using unpaired Student's t-test ($p<0.01$) or ANOVA. Gao C F, Vande Woude G F, "HGF/SF-Met signaling in tumor progression." Cell Res. 15: 49-51, 2005; Christensen J G, et al., Cancer Res. 63: 7345-7355, 2003; Milne G W, et al., J Chem Inf Comput Sci. 36: 726-30, 1996.

Figure 4A:
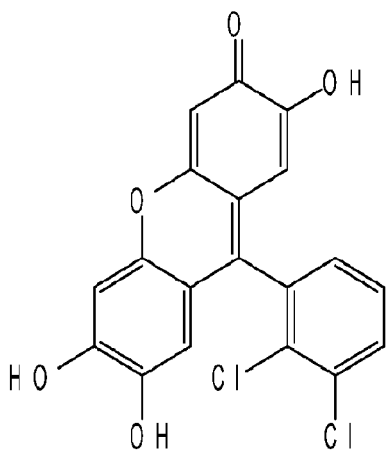
FIGS. 4A, 4B, and 4C show structure and activity of compound 30267662.

Compound 30267662 was identified in a screen of all 70 available compounds using the cell-free assay for c-Met kinase inhibition (FIG. 4A). The nature of this assay virtually precludes the identification of agents that act indirectly through proteins other than c-Met, suggesting that this compound binds directly to the c-Met ATP binding site. Results of experiments performed across a range of ATP concentrations further support direct competitive antagonism of ATP binding by compound 30267662. The inclusion of non-ionic detergent through the assay procedure also suggests that inhibition is not due to promiscuous effects of compound aggregation. Feng B Y, Shoichet B K, Nature Protocols 1: 550-551, 2006.

Figure 4B:
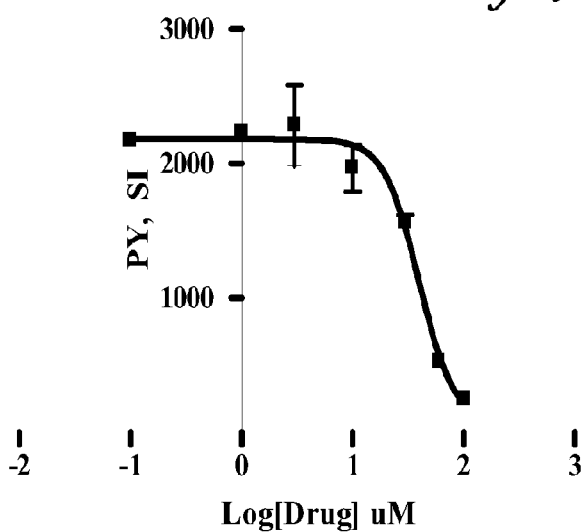
Figure 4C:
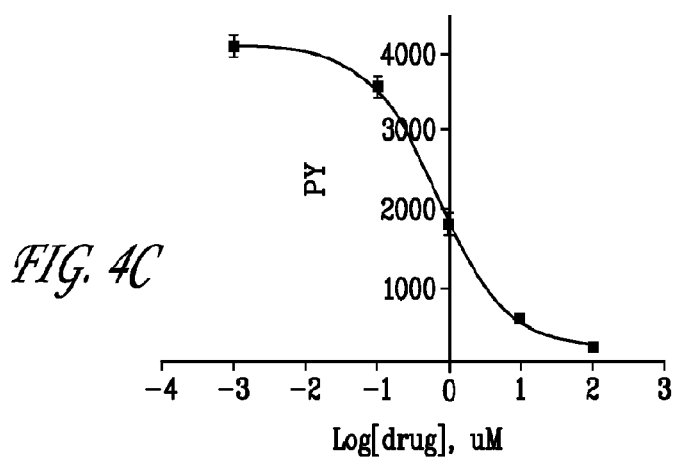
Figure 5A:
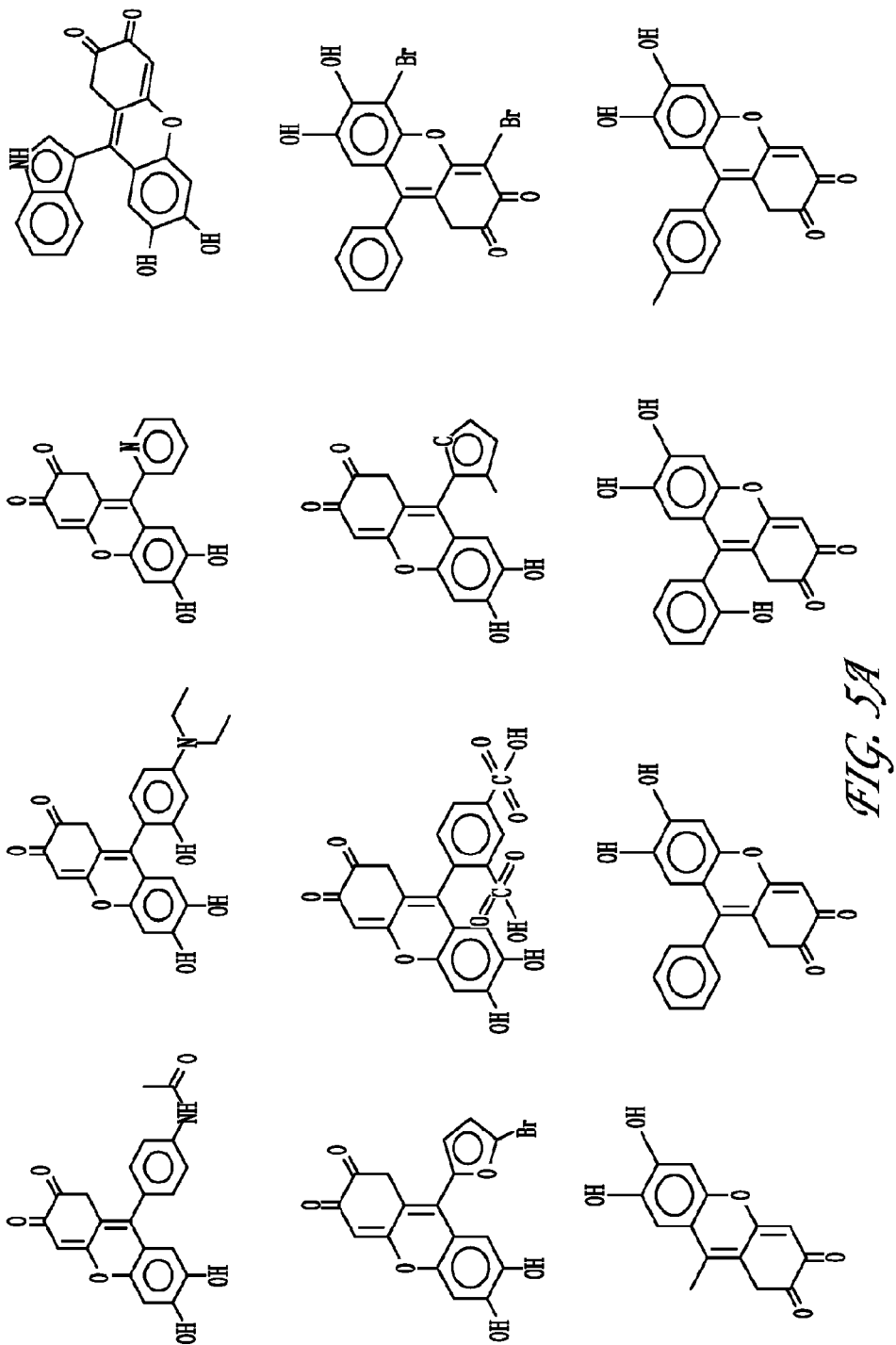
FIGS. 5A, 5B, and 5C show structures of analogs of compound 30267662.
Figure 5B:
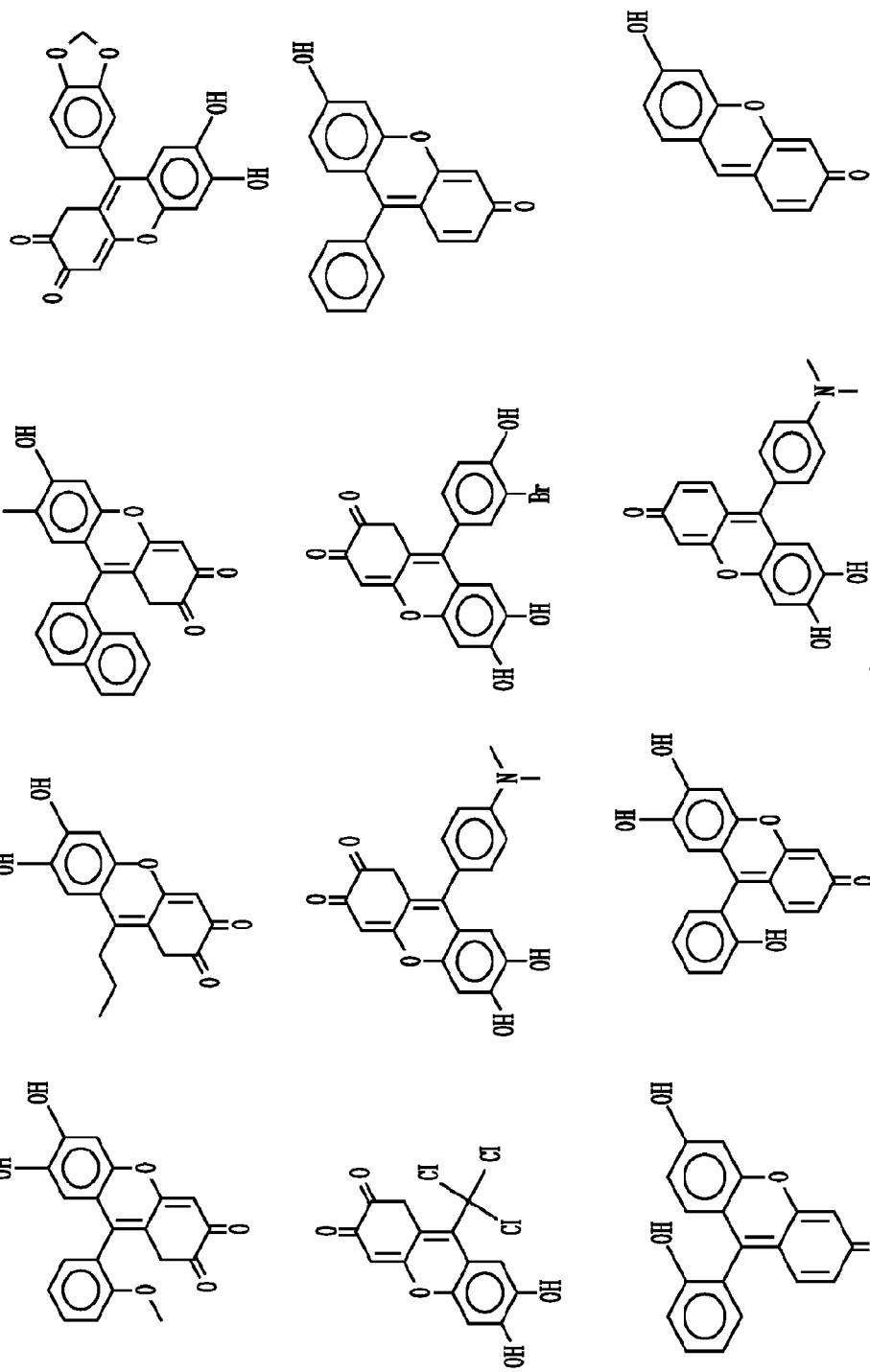
Figure 5C:
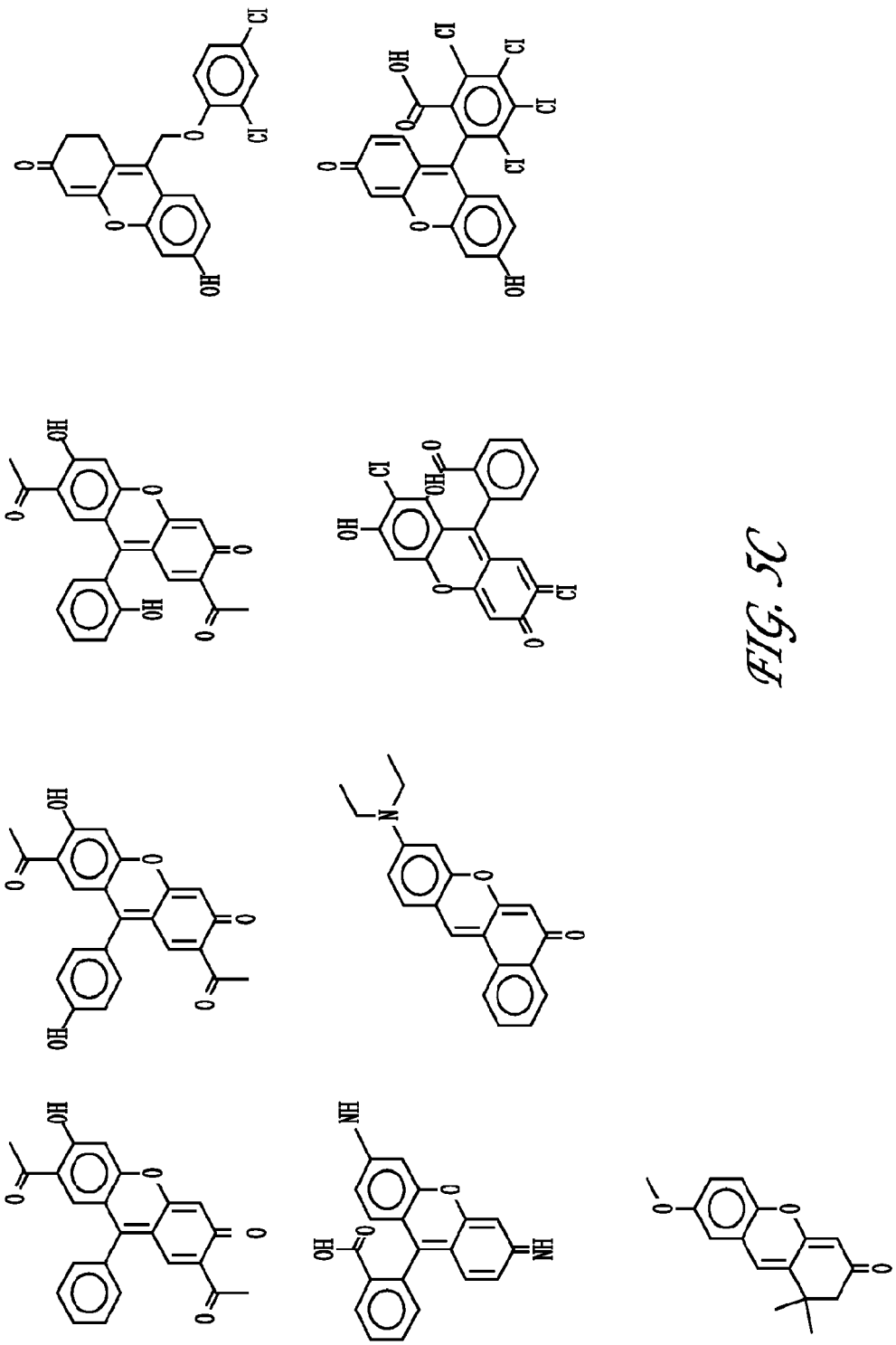
Figure 6A:
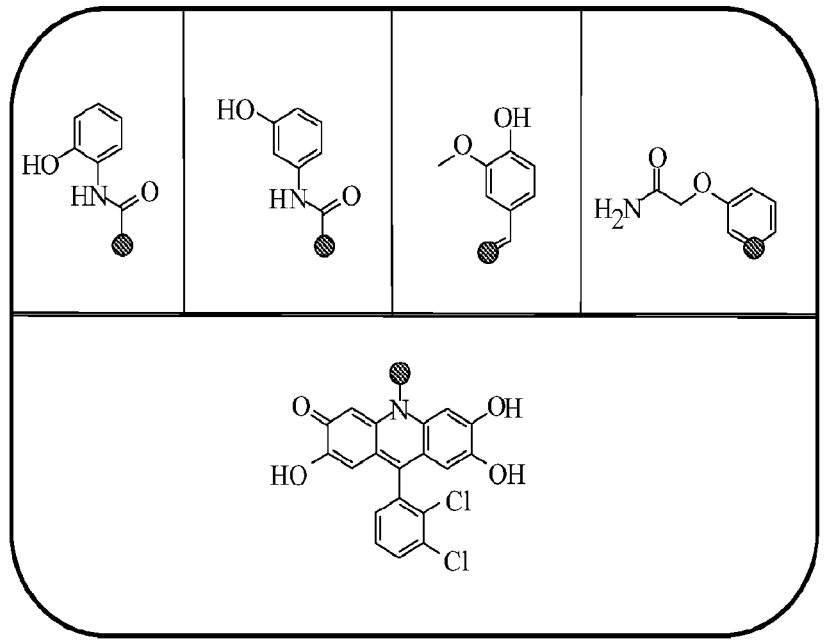
FIGS. 6A, 6B, 6C, 6D, 6E, and 6F show structures of analogs of compound 30267662.
Figure 6B:
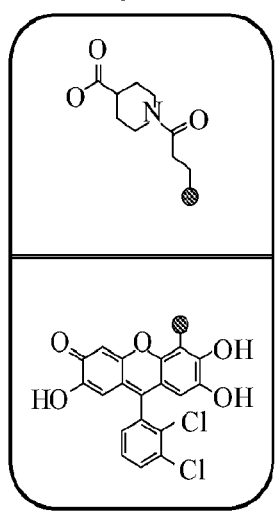
Figure 6C:
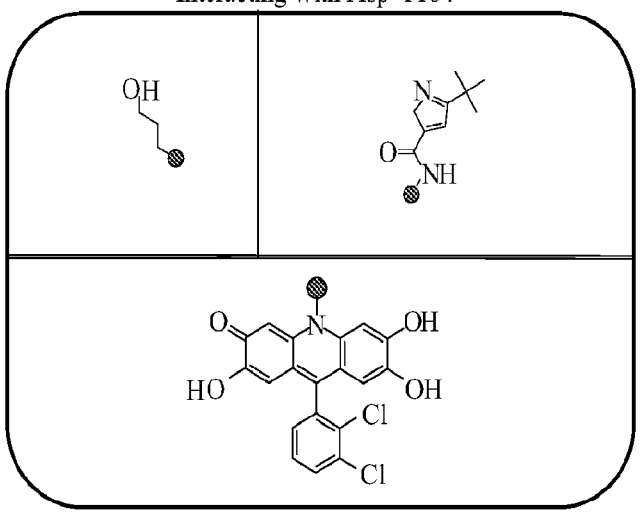
Figure 6D:
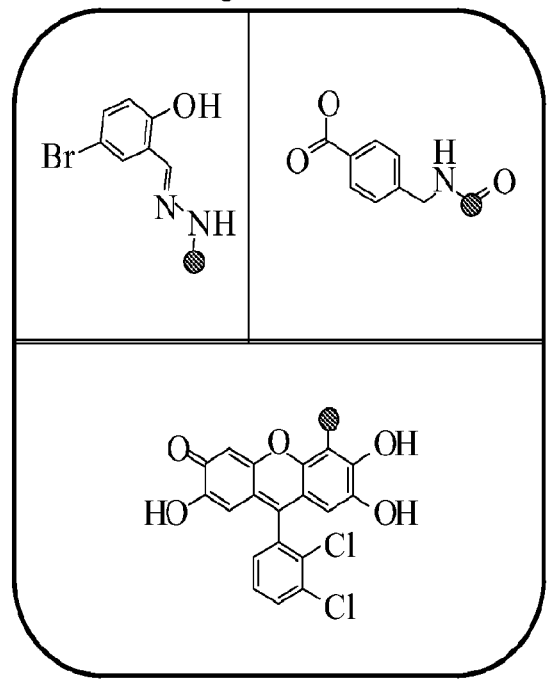
Figure 6E:
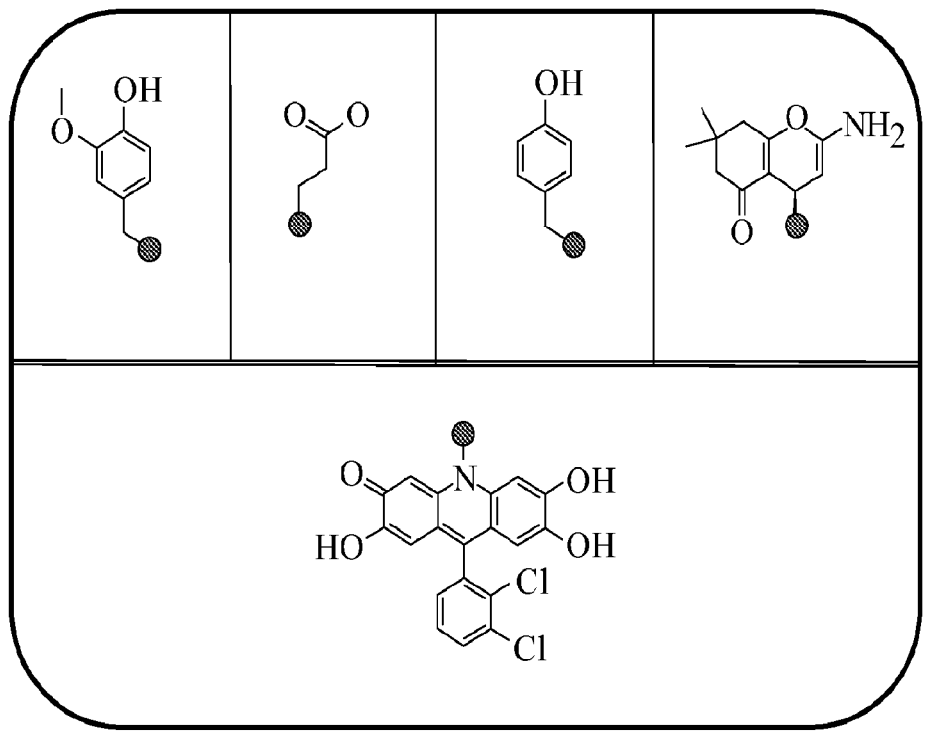
Figure 6F:
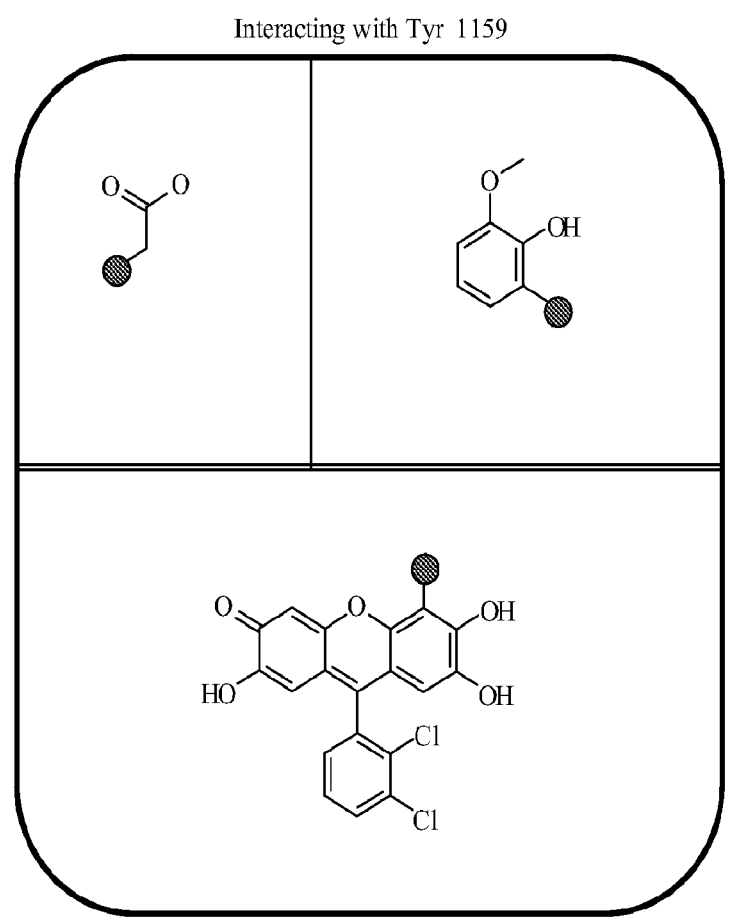

The chemical structure and physical properties of compound 30267662 indicate that it is distinct from other known kinase inhibitors (FIG. 4A). Regression analysis of the dose response of c-Met TK inhibition in cell-free conditions yielded an estimated IC50 of ~0.675 µM ($R2=0.995$; FIG. 4B). Follow-up analysis of this compound for c-Met inhibition in intact B5/589 cells also revealed a dose-dependent effect, with an estimated IC50 of ~30 µM ($R2=0.92$; FIG. 4C). No reduction in c-Met expression or total cellular protein (an index of cytotoxicity) was detected under these conditions.

FIG. 4 shows structure and activity of compound 30267662 (9-(2,3-Dichloro-phenyl)-2,6,7-trihydroxy-xanthen-3-one). A. Chemical structure and physical properties. B. Dose response of inhibition of cell-free c-Met autophosphorylation. $IC_{50}$ estimated by regression analysis is 0.675 µM, $R^2=0.995$. C. Dose response of inhibition of c-Met autophosphorylation in intact B5/589 cells, corrected for total protein concentration. $IC_{50}$ estimated by regression analysis is ~30 µM, $R^2=0.99$. No reduction in c-Met expression was detected in intact cells, nor was any cytotoxicity detected as indicated by loss of total cell protein.

Example 3

Selectivity Assessment of Lead Compound 30267662

The submicromolar potency of compound 30267662 for inhibition of c-Met ATP binding and autophosphorylation prompted us to investigate the activity of this against other structurally related, oncogenically relevant TKs. A panel of 10 TKs: ABL1, ALK. EGFR, FGFR1, IGF1R, VEGFR2, c-Met, RON, PDGFR beta and ROS1, was selected for analysis through the SelectScreen Kinase Profiling Service (Invitrogen, Carlsbad, Calif.). The assay method employs a fluorescence-based, coupled-enzyme format and is based on the differential sensitivity of phosphorylated and non-phosphorylated peptides to proteolytic cleavage. A significant benefit of this ratiometric method for quantitating reaction progress is the elimination of well-to-well variation in peptide concentration and signal intensities. The results of this analysis are summarized in Table 1. Significant inhibition (>50%) at 10 µM compound 30267662 was observed for c-Met, VEGFR2, ABL1, and FGFR1, with greatest relative inhibition of FGFR1 Inhibitory activity on VEGFR2 has been reported for other c-Met TK inhibitors such as PHA665752 and SU11274 (Salgia and Christensen, 2005). The potent inhibitory effect on FGFR1, an important mediator of angiogenesis, could prove to be very desirable feature of a small molecule c-Met antagonist. FGFR1-mediated signaling has been implicated in the progression of a wide variety of solid tumor types where c-Met activation also occurs, including pancreatic and thyroid cancers. Liu et al., Can Res 67: 2712-9, 2007, Kondo et al., Can Res 67: 5461-70, 2007. FGFR1 gene amplification occurs in breast cancer, Elbauomy et al., Breast Cancer Res 9: R23, 2007, and overexpression occurs in the majority of high-grade prostate cancers. Sahadevan et al., J Pathol 213: 82-90, 2007. Another agent with combined activity on VEGFR2 and FGFR1, brivanib alaninate (Bristol-Myers Squibb) is currently in clinical trials. Ayers et al., Can Res 76: 6899-906, 2007.

TABLE 1

Preliminary TK selectivity profile of compound 30267662

| Kinase Tested | % Inhibition at 10 µM mean |
|---|---|
| ABL1 | 60 |
| ALK | 36 |
| EGFR (ErbB1) | 14 |
| FGFR1 | 85 |
| IGF1R | −7 |
| KDR (VEGFR2) | 73 |

TABLE 1-continued

Preliminary TK selectivity profile of compound 30267662

| Kinase Tested | % Inhibition at 10 μM mean |
|---|---|
| MET (cMet) | 55 |
| MST1R (RON) | 45 |
| PDGFRB (PDGFR beta) | 8 |
| ROS1 | 27 |

When ranges are used herein for physical properties, such as molecular weight, or chemical properties, such as chemical formulae, all combinations and subcombinations of ranges and specific embodiments therein are intended to be included.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

REFERENCES

All publications and patent applications cited in this specification are herein incorporated by reference in their entirety for all purposes as if each individual publication or patent application were specifically and individually indicated to be incorporated by reference for all purposes

We claim:

1. A compound that is 9-(2,3-dichloro-phenyl)-2,6,7-trihydroxy-xanthen-3-one, or a pharmaceutically acceptable salt thereof.

2. A pharmaceutical composition comprising at least one pharmaceutically acceptable carrier or excipient and 9-(2,3-dichloro-phenyl)-2,6,7-trihydroxy-xanthen-3-one.

3. A method for treating a mammal having a neoplastic disease,
wherein the treatment delays the onset of symptoms, complications, or biochemical indicia of the disease; alleviates the symptoms of the disease, arrests further development of the disease; or inhibits further development of the disease;
wherein the neoplastic disease is characterized by a c-Met mutation or an overexpression of c-Met, comprising administering to the mammal a therapeutically effective amount of a compound of Formula I:

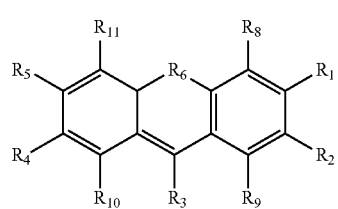

I or a pharmaceutically acceptable salt thereof,
wherein
$R_1$ and $R_2$ are each independently H, —CN, S, O, N, F, —CH$_2$—OH, —OH, C$_1$-C$_4$ alkyl, amine, or ethanone, and at least one of $R_1$ and $R_2$ is —CN, S, O, N, or F;
$R_3$ is H; C$_1$-C$_4$ alkyl optionally substituted with halo or sulfonate; phenyl, phenoxy, or phenoxyalkyl, each optionally substituted with one or two substituents selected from hydroxyl, alkoxy, alkyl, halo, acetamido, acetamido alkoxy, carboxyl, and optionally-substituted amino; indolyl; pyridinyl; furanyl; thiophenyl; benzo[1,3]dioxolyl; or morpholinoalkyl, phenylalkyl or naphthylalkyl, each optionally substituted with alkyl, halo, or haloalkyl;
$R_4$ and $R_5$ are each independently H; —CN; S; O; N; F; OH; C$_1$-C$_4$ alkyl; amine; ethanone; phenyl optionally substituted with hydroxyl, alkyl, or halo; or morpholinoalkyl, and at least one of $R_4$ and $R_5$ is —CN, S, O, N, F, or OH;
$R_6$ is O or N—$R_7$; and
$R_7$ and $R_8$ are each independently H; C$_1$-C$_4$ alkyl; hydroxyalkyl; carboxyalkyl; phenyl optionally substituted with one or more substituent selected from hydroxyl, alkoxy, carboxyl, halo, and acetamide-oxy; phenylamido; phenylamido carboxyl; phenylalkyl; phenylalkenyl; phenylhydrazonoalkyl; morpholinoalkyl; piperidine-proprionyl optionally substituted with carboxyl; or chromen-5-one optionally substituted with alkyl, dialkyl, or amino; and
$R_9$, $R_{10}$, and $R_{11}$ are each independently H, lower alkyl, or halo.

4. The method of claim 3 wherein $R_6$ is O and $R_8$ is piperidine-proprionyl optionally substituted with carboxyl.

5. The method of claim 3 wherein $R_1$ is O and $R_2$ is OH.

6. The method of claim 3 wherein $R_4$ and $R_5$ are each OH.

7. The method of claim 3 wherein $R_3$ is phenyl substituted with two halogen atoms.

8. The method of claim 3 wherein the halogen atoms are Cl, Br, F, or I.

9. The method of claim 3 wherein the compound acts through c-Met protein down-regulation and TK inhibition.

10. The method of claim 3 wherein the compound inhibits TK activity as a competitive ATP binding antagonist.

11. The method of claim 3 wherein:
$R_1$ is =O,
$R_2$, $R_4$, and $R_5$ are each OH,
$R_3$ is phenyl di-substituted with chloro,
$R_6$, is O, and
$R_8$, $R_9$, $R_{10}$, and $R_{11}$ are each H.

12. The method of claim 3 comprising administering a therapeutically effective amount of 9-(2,3-dichloro-phenyl)-2,6,7-trihydroxy-xanthen-3-one, or a pharmaceutically acceptable salt thereof.

13. The method of claim 3, wherein the neoplastic disease is renal cell carcinoma, lung cancer, thyroid cancer, or head and neck cancer.

* * * * *

UNITED STATES PATENT AND TRADEMARK OFFICE
CERTIFICATE OF CORRECTION

PATENT NO.        : 8,569,360 B2                                    Page 1 of 1
APPLICATION NO.   : 12/935646
DATED             : October 29, 2013
INVENTOR(S)       : Bottaro et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this
Twenty-second Day of September, 2015

Michelle K. Lee
*Director of the United States Patent and Trademark Office*